(12) United States Patent
Verhaert et al.

(10) Patent No.: US 8,080,198 B2
(45) Date of Patent: Dec. 20, 2011

(54) ELASTIC DIAPER COMPONENT

(75) Inventors: Anne Verhaert, Vorselaar (BE); Martin Westerhuis, Valkenswaard (NL)

(73) Assignee: Avery Dennison Corporation, Pasadena, CA (US)

( * ) Notice: Subject to any disclaimer, the term of this patent is extended or adjusted under 35 U.S.C. 154(b) by 292 days.

(21) Appl. No.: 12/160,440

(22) PCT Filed: Aug. 31, 2007

(86) PCT No.: PCT/US2007/077349
§ 371 (c)(1),
(2), (4) Date: Jul. 10, 2008

(87) PCT Pub. No.: WO2008/028106
PCT Pub. Date: Mar. 6, 2008

(65) Prior Publication Data
US 2009/0008023 A1    Jan. 8, 2009

Related U.S. Application Data

(66) Substitute for application No. 60/824,261, filed on Aug. 31, 2006.

(60) Provisional application No. 60/862,252, filed on Oct. 20, 2006, provisional application No. 60/912,983, filed on Apr. 20, 2007, provisional application No. 60/913,059, filed on Apr. 20, 2007, provisional application No. 60/913,048, filed on Apr. 20, 2007, provisional application No. 60/941,402, filed on Jun. 1, 2007, provisional application No. 60/941,420, filed on Jun. 1, 2007, provisional application No. 60/941,431, filed on Jun. 1, 2007.

(51) Int. Cl.
*B32B 38/04* (2006.01)

(52) U.S. Cl. .................................. 264/290.2; 264/289.3
(58) Field of Classification Search ............... 156/173.3, 156/73.3; 264/289.3, 290.2
See application file for complete search history.

(56) References Cited

U.S. PATENT DOCUMENTS

| | | |
|---|---|---|
| 829,805 A | 8/1906 | Sackville |
| 2,473,404 A | 6/1949 | Young |
| 2,618,012 A | 11/1952 | Milne |
| 2,626,422 A | 1/1953 | Lammertse |

(Continued)

FOREIGN PATENT DOCUMENTS

| DE | 37 10 037 | 3/1987 |
|---|---|---|

(Continued)

OTHER PUBLICATIONS

International Search Report and Written Opinion issued in corresponding PCT/US2007/077367 dated Dec. 4, 2007.

(Continued)

*Primary Examiner* — Joseph Del Sole
*Assistant Examiner* — Kimberly A Stewart

(57) ABSTRACT

A method of making an elastic component for incorporation into a diaper. The elastic diaper component begins as an elastic laminate (e.g., an elastic layer and a fabric layer) having a recoverable extension of at least 20% when an extension force $E_1$ is applied. The method comprises the step of integratively pre-stretching the elastic laminate so that the elastic laminate will stretch to the same recoverable extension when a reduced extension force $E_2$ is applied. In this manner, when the elastic laminate is used in the elastic diaper component, a lesser fitting force $F_{fit}$ is required to extend the elastic component to a desired length during an initial fitting of a diaper on a wearer.

14 Claims, 17 Drawing Sheets

U.S. PATENT DOCUMENTS

| | | |
|---|---|---|
| 2,841,820 A | 7/1958 | Pfeiffer |
| 3,078,504 A | 2/1963 | Koppehele |
| 3,193,873 A | 7/1965 | Wienand |
| 3,261,903 A | 7/1966 | Carr |
| 3,296,351 A | 1/1967 | Ole-Bendt Rasmussen |
| 3,577,586 A | 5/1971 | Kalwaites |
| 3,719,540 A | 3/1973 | Hall |
| 3,800,796 A | 4/1974 | Jacob |
| 3,833,973 A | 9/1974 | Schwarz |
| 3,949,127 A | 4/1976 | Ostermeier et al. |
| 4,063,559 A | 12/1977 | Tritsch |
| 4,116,892 A | 9/1978 | Schwarz |
| 4,389,212 A | 6/1983 | Tritsch |
| 4,643,729 A | 2/1987 | Laplanche |
| 4,731,066 A | 3/1988 | Korpman |
| 4,787,897 A | 11/1988 | Torimae et al. |
| 4,795,456 A | 1/1989 | Borgers et al. |
| 4,862,564 A | 9/1989 | Kwack |
| 4,968,313 A | 11/1990 | Sabee |
| 5,038,989 A | 8/1991 | Beliveau |
| 5,057,097 A | 10/1991 | Gesp |
| 5,072,493 A | 12/1991 | Hommes et al. |
| 5,143,679 A | 9/1992 | Weber et al. |
| 5,156,793 A | 10/1992 | Buell et al. |
| 5,167,897 A | 12/1992 | Weber et al. |
| 5,344,691 A | 9/1994 | Hanschen et al. |
| 5,468,428 A | 11/1995 | Hanschen et al. |
| 5,628,097 A | 5/1997 | Benson et al. |
| 5,729,878 A * | 3/1998 | Kurihara et al. ............... 26/101 |
| 5,791,030 A * | 8/1998 | Aihara et al. ..................... 26/87 |
| 5,804,021 A * | 9/1998 | Abuto et al. .................. 156/252 |
| 5,804,286 A * | 9/1998 | Quantrille et al. ............ 428/198 |
| 5,916,661 A | 6/1999 | Benson et al. |
| 6,069,097 A | 5/2000 | Suzuki et al. |
| 6,420,285 B1 * | 7/2002 | Newkirk et al. .............. 442/364 |
| 6,461,715 B1 | 10/2002 | Guenther et al. |
| 6,551,436 B1 | 4/2003 | Flohr et al. |
| 6,632,504 B1 | 10/2003 | Gillespie et al. |
| 6,712,921 B2 | 3/2004 | Mitsuno et al. |
| 7,001,475 B2 | 2/2006 | Ausen et al. |
| 7,135,213 B2 | 11/2006 | Maki et al. |
| 2003/0089454 A1 * | 5/2003 | Johnson ..................... 156/308.2 |
| 2003/0105446 A1 | 6/2003 | Hutson et al. |
| 2003/0124291 A1 | 7/2003 | Ausen et al. |
| 2005/0025937 A1 | 2/2005 | Maki et al. |
| 2005/0215972 A1 | 9/2005 | Roe et al. |
| 2005/0249915 A1 | 11/2005 | Wood et al. |
| 2006/0148359 A1 | 7/2006 | Van Gompel et al. |
| 2007/0040000 A1 | 2/2007 | Jackson et al. |
| 2007/0040301 A1 | 2/2007 | Jackson |
| 2007/0105472 A1 | 5/2007 | Marche |
| 2008/0045107 A1 * | 2/2008 | Michalon et al. ............. 442/335 |

FOREIGN PATENT DOCUMENTS

| | | |
|---|---|---|
| DE | 19522743 | 12/1996 |
| DE | 196 47 459 | 5/1998 |
| DE | 196 474 59 * | 5/1998 |
| EP | 0190355 | 8/1986 |
| EP | 0 596 532 | 5/1994 |
| EP | 0936061 | 8/1999 |
| EP | 1277868 | 1/2003 |
| WO | 9610481 | 4/1996 |

OTHER PUBLICATIONS

International Preliminary Report on Patentability issued in corresponding PCT/US2007/077367 dated Mar. 12, 2009.

International Preliminary Report on Patentability issued in corresponding PCT/US2007/077349 dated Mar. 12, 2009.

International Search Report and Written Opinion issued in corresponding PCT/US2007/077359 dated Dec. 4, 2007.

International Preliminary Report on Patentability issued in corresponding PCT/US2007/077359 dated Jan. 20, 2009.

PCT/US2007/077349; PCT International Search Report dated Jun. 4, 2008.

* cited by examiner

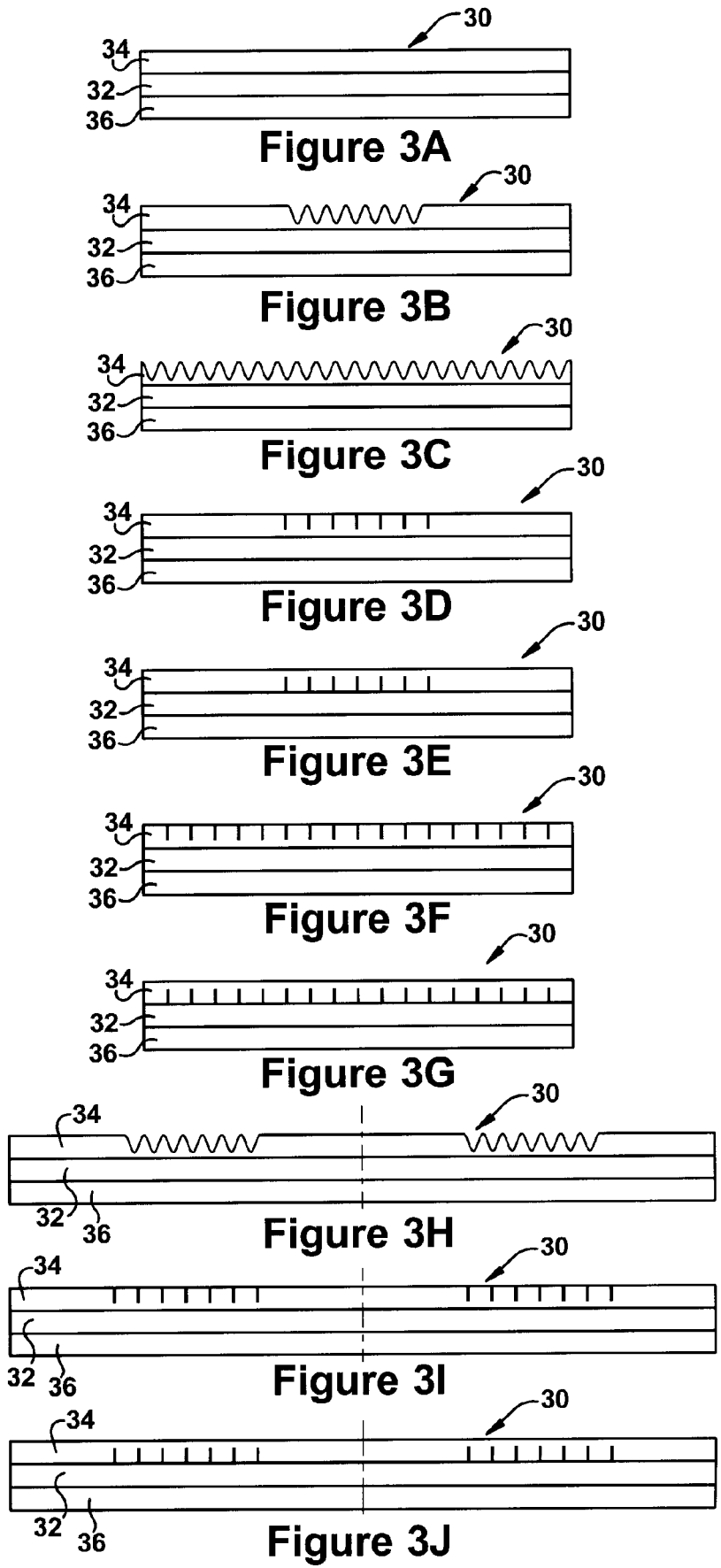

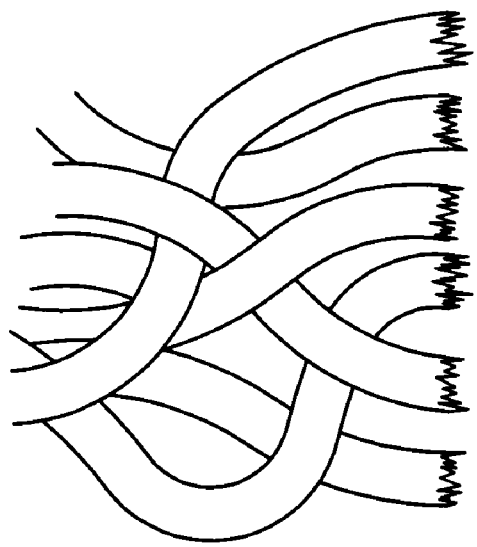 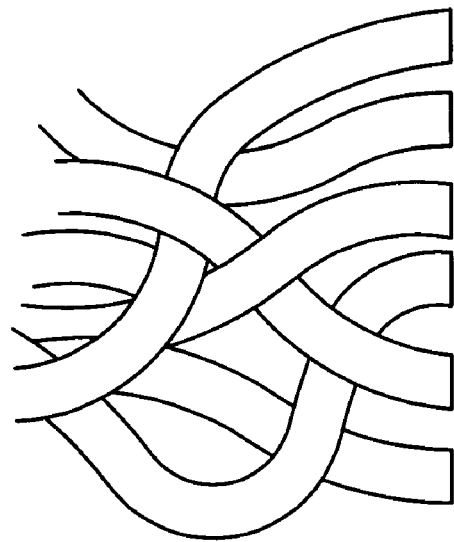
Figure 12A                    Figure 12B

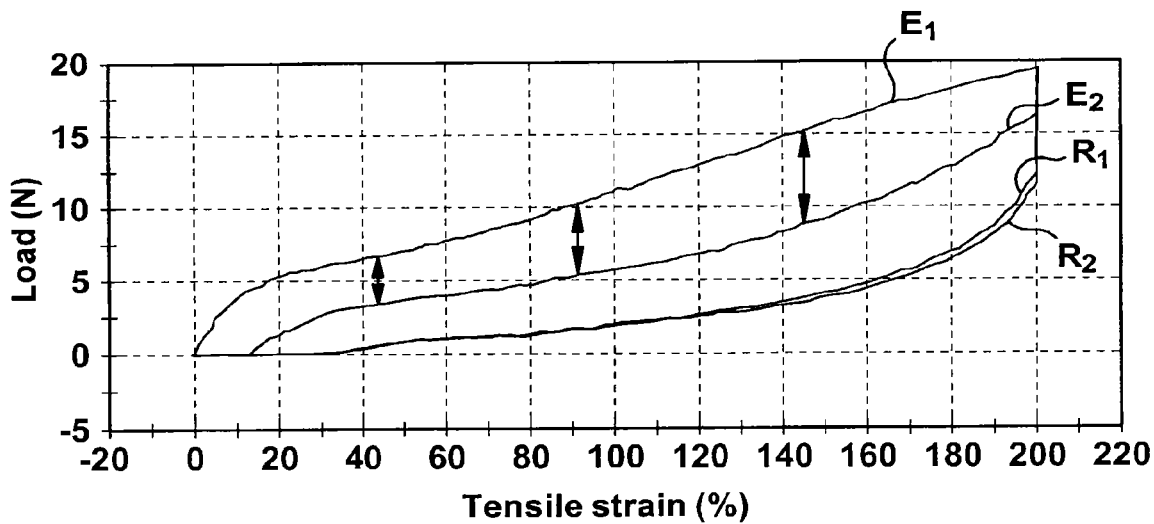
GRAPH 1
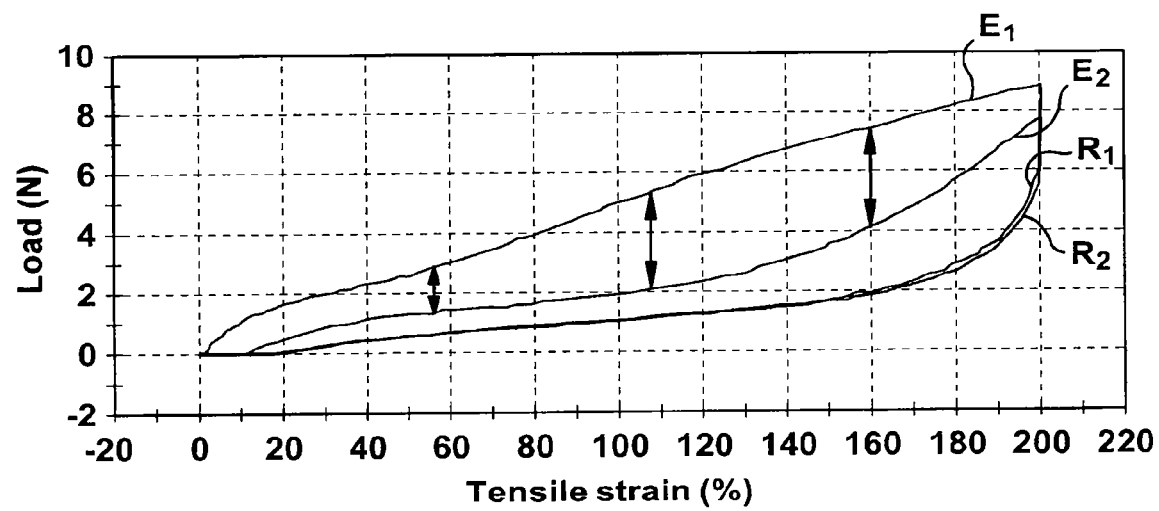
GRAPH 2

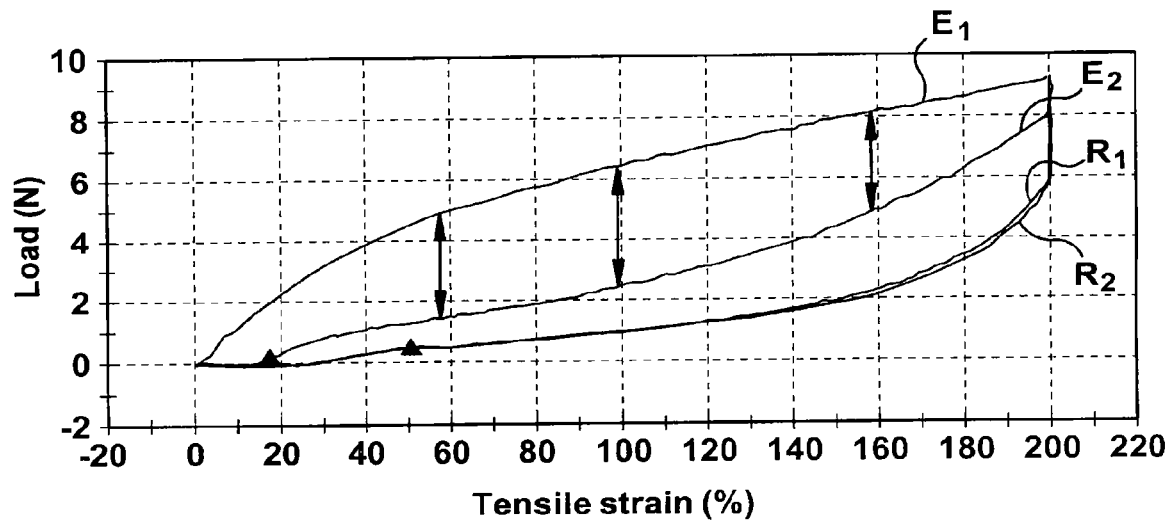
GRAPH 3
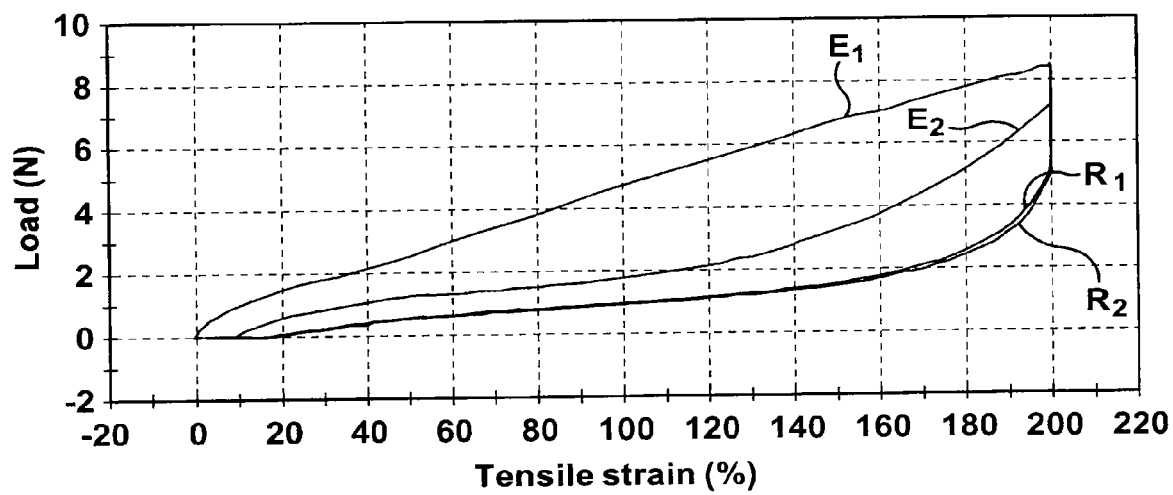
GRAPH 4

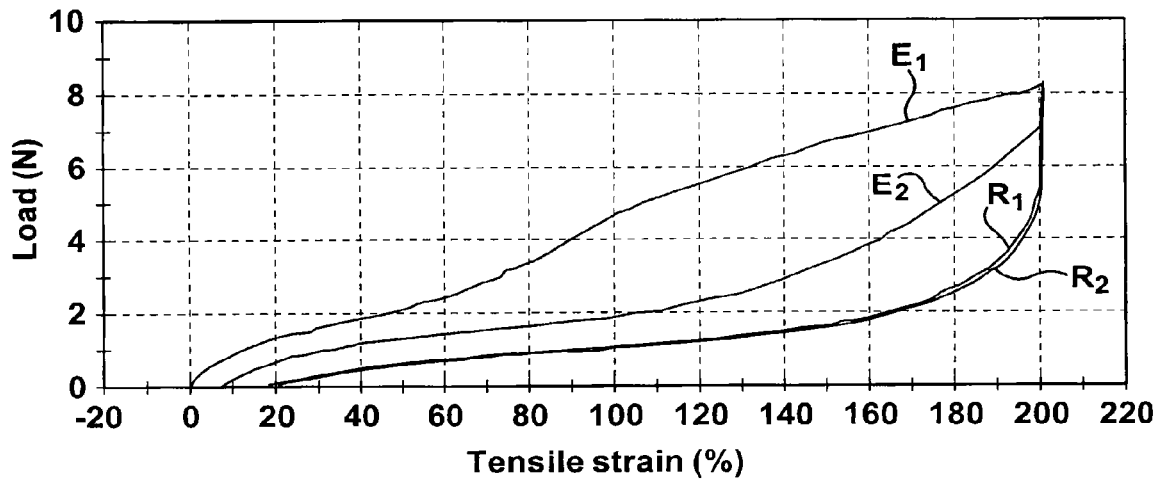
GRAPH 5
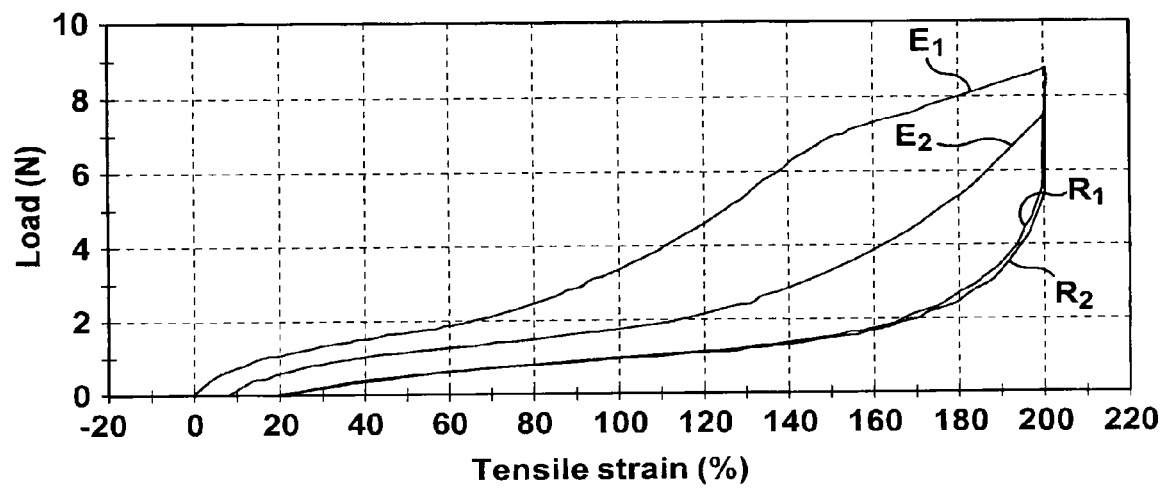
GRAPH 6

ELASTIC DIAPER COMPONENT

This application is a national phase of International Application No. PCT/US2007/077349, filed Aug. 31, 2007, which claims priority to U.S. Provisional Application Ser. No. 60/941,420 filed Jun. 1, 2007, U.S. Provisional Application Ser. No. 60/912,983 filed Apr. 20, 2007, U.S. Provisional Application Ser. No. 60/862,252 filed Oct. 20, 2006, and other provisional applications. The entire disclosure of this international application and the entire disclosure of these priority provisional applications are hereby incorporated by reference.

A diaper commonly comprises a chassis having a front portion, a rear portion, and a crotch portion therebetween. When diapering a wearer, the crotch portion is placed between his/her legs and the rear portion is fastened, via a fastener, to the front portion to form a waist around the wearer. The fastener can be carried by a fastening tape component secured to the respective lateral edge of the rear chassis portion, or the fastener can be carried by a side panel component or belt component secured to this lateral edge.

Fastening tape components, side panel components, and/or belt components are often components comprising an elastic laminate (e.g., a laminate having a recoverable extension of at least 20% when an extension force E is applied). During the diapering process, the elastic component is stretched (e.g., it is pulled by the parent of the to-be-diapered baby) at a force $F_{fit}$ to an extended length and the fastener is fastened to the front chassis portion or an appendage thereof. Once fastening is accomplished, and the fitting force $F_{fit}$ is released, the inherent recovery retraction force of the elastic component causes it to retract thereby snugly securing the diaper around the wearer's waist. As the wearer's belly expands and contracts during use of the diaper, the elastic component extends and retracts to comfortably accommodate this movement while maintaining the snug fit of the diaper.

SUMMARY

An elastic diaper component (e.g., a side panel component, a fastening tape component, and/or a belt component) comprises an elastic laminate which initially has a recoverable extension of at least 20% when stretched at an extension force $E_1$. This elastic laminate is subjected to integrative pre-stretching to thereby allow the elastic laminate to be stretched to the same recoverable extension at a reduced extension force $E_2$. In this manner, when the elastic laminate is used as an elastic diaper component, the force reduction instilled by the integrative pre-stretching step lowers the fitting force $F_{fit}$ (e.g., the magnitude of the "pull") necessary to extend the component to a desired length during fitting of a diaper. Also, the pre-stretching decreases the extension force necessary to accommodate the expansion of the wearer's belly (or other conditions increasing waist circumference) during use of the diaper.

The recovering retraction forces $R_2$ of the pre-stretched elastic laminate can be substantially the same as the recovering retraction force $R_1$ of the original laminate (i.e., the elastic laminate prior to the pre-stretching step). Thus, the pre-stretched elastic component can retract in much the same manner as the original elastic laminate. In this manner, the pre-stretched component can appropriately retract to accommodate contraction of the wearer's belly (or other conditions decreasing waist circumference) during use of the diaper.

In an original elastic laminate (i.e., an elastic laminate prior to or without pre-stretching), the extension force often increases substantially linearly from minimum to maximum extension. With the pre-stretched component, the extension force increases substantially linearly in early/intermediate stages of material extension and then inclines more sharply in the longer stages of material extension. There will be a sudden increase in resistance when the elastic laminate is stretched beyond the intermediate lengths and, when the person fitting the diaper feels this resistance, his/her reflexive reaction is usually to cease elongation of the component. Thus, pre-stretched elastic laminate can guard against over-extension of the component during the diapering process. Also, the linear (gradual) region of extension forces often corresponds to the linear regions of the retraction forces, whereby they will be gradual (as opposed to sudden and snap-like) retraction during diaper use.

With the pre-stretched diaper component, the elastic qualities of the original laminate will be enhanced (e.g., the force required to stretch to a recoverable extension will be reduced) prior to use of the diaper. This allows the sometimes stringent specifications imposed on elastic laminates to be matched more easily. Thanks to the integrative pre-stretching step, a wider range of elastic laminates (and perhaps more economical laminates) will qualify as suitable candidates for the production of elastic diaper components.

With particular reference to activated elastic laminates (e.g., laminates which achieve elasticity upon incremental stretching of inelastic nonwoven layers), an integrative pre-stretching (post-activation) step provides the welcome option of less aggressive activation. For example, with a ring rolling method, the groove pitch of the incremental-strain-imposing rollers need not be as deep as would be necessary to achieve the same fitting force $F_{fit}$ characteristics without integrative pre-stretching. This less destructive approach can decrease the risk of material damage (e.g., the creation of weak spots in the elastic layer that are susceptible to tearing or breaking) during activation. On this same note, the use of integrative pre-stretching techniques (as opposed to incremental pre-stretching techniques) eliminates the disadvantages and dangers associated with localized and/or discrete strain imposition. That being said, such integrative pre-stretching techniques may be suitable for situations wherein rupturing of a fabric layer is desired to create, for example, fabric segments which diverge upon laminate elongation and converge upon laminate recovery.

DRAWINGS

FIGS. 2A-2J, FIGS. 3A-3J, FIGS. 4A-4I, FIGS. 5A-5H and FIGS. 6A-6H are side schematic views of some of the possible elastic laminates that can be used in elastic diaper components.

FIGS. 12A and 12B are schematic magnified representations of a ruptured region and a severed region, respectively.

GRAPHS

Figure 1A:
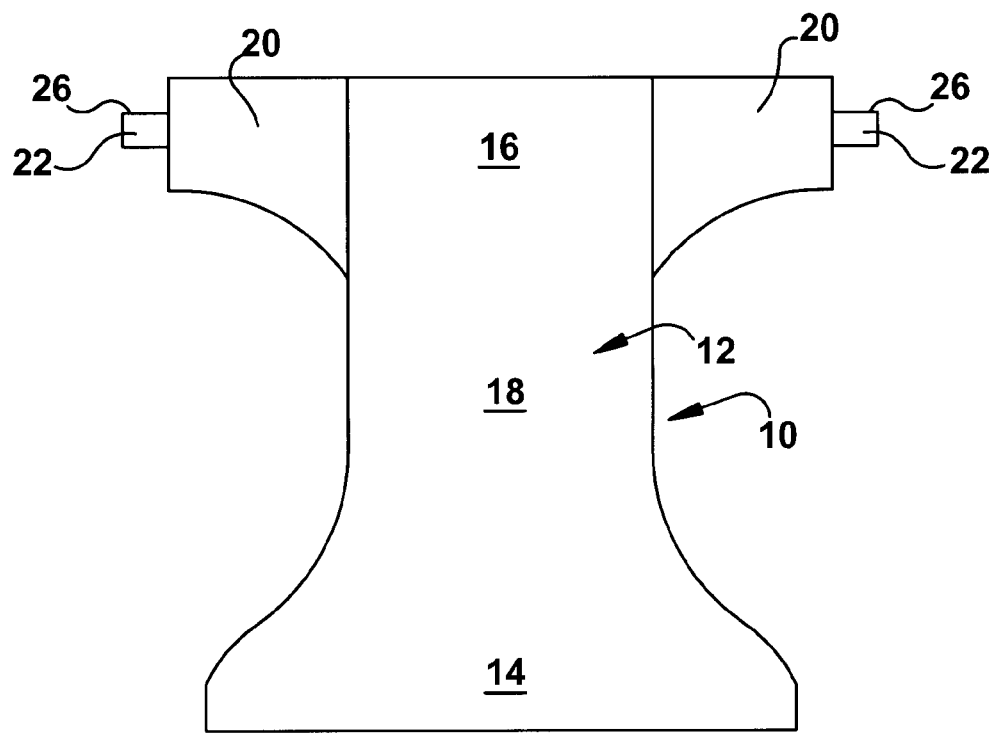
FIGS. 1A-1F are plan schematic views of some of the possible diaper designs incorporating pre-stretched elastic components (e.g., side panel components, fastening tape components, and/or belt components).

Graphs 1-3 each are plots of extension forces E and retraction forces R for three different elastic laminate constructions, respectively.

Graphs 4-6 are each plots of extension forces E and retraction forces R for the same elastic laminate construction with differing degrees of pre-stretching.

The hysteresis tests used to obtain the data for the graphs were performed on a tensile tester with a load cell 100 N, a cross head speed of 300 mm/m, an initial clamp separation of 30 mm, and a maximum cross head position of 60 mm. Test samples each had a width of 25 mm and a minimum length of 50 mm, and were conditioned for at least 24 hours at 23° C. (±2° C.) and relative humidity of 50%. During the testing, the cross head moved the sample (clamped in the grips of the tensile tester) to a predetermined maximum position, held the sample in this position for 30 seconds, and released the retaining force allowing the sample to retract. A subsequent cycle began after the sample rested in its retracted condition for 30 seconds.

DETAILED DESCRIPTION

Referring now to the drawings, and initially to FIGS. 1A-1F, a diaper 10 can comprise a chassis 12 having a front portion 14, a rear portion 16, and a crotch portion 18 therebetween. The diaper chassis 12 can include a liquid permeable topsheet, a liquid impermeable backsheet, and an absorbent core interposed therebetween. The diaper 10 can be made, for example, in smaller sizes for a baby or child, and/or in larger sizes for an adult. The term "diaper" as used in this specification refers to an absorbent article worn around the waist of a wearer for the purpose of collecting body fluids. The diaper can be a disposable article intended to be used until soiled and then discarded. Alternatively, the diaper can be a reusable article adapted to be washed and used again.

Figure 1B:
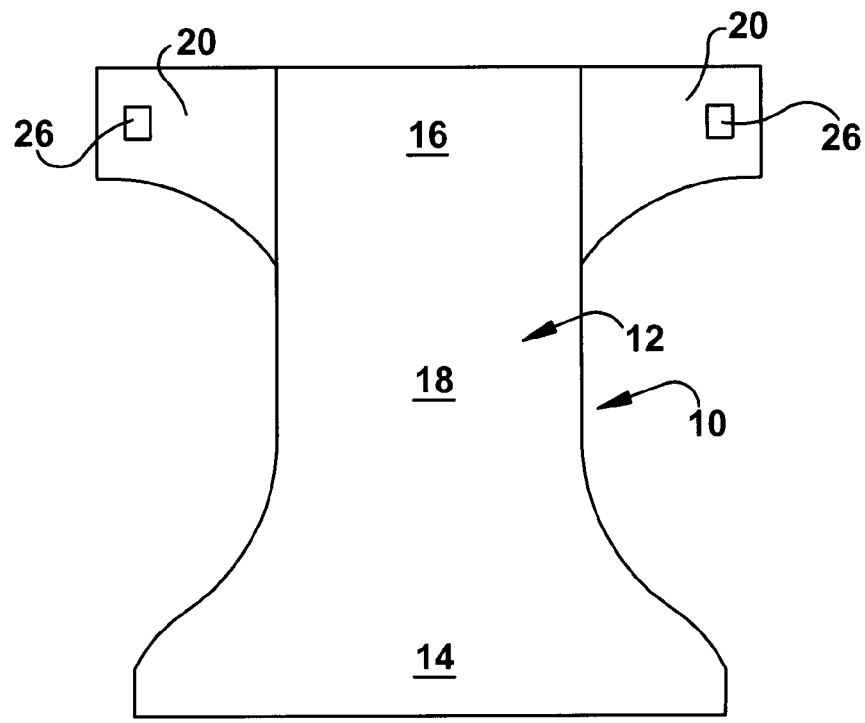
Figure 1C:
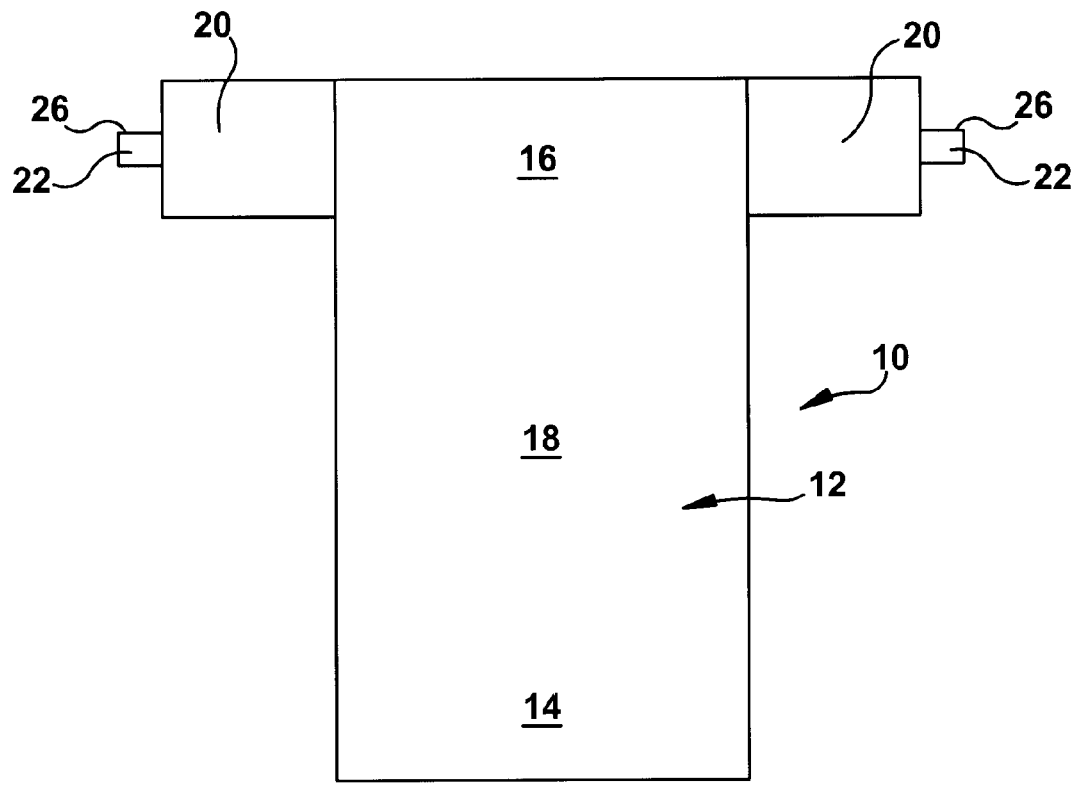

The diaper 10 can include a side panel component 20 attached to each lateral edge of the chassis rear portion 16 (FIGS. 1A-1D). The side panel shape can include a curved lower edge (FIGS. 1A and 1B), can be rectangular (FIGS. 1C and 1D), and/or any other suitable geometry. A fastening tape component 22, can extend outward from side panel component 20 and carry a fastener 26 thereon (FIGS. 1A and 1C).

Figure 1D:
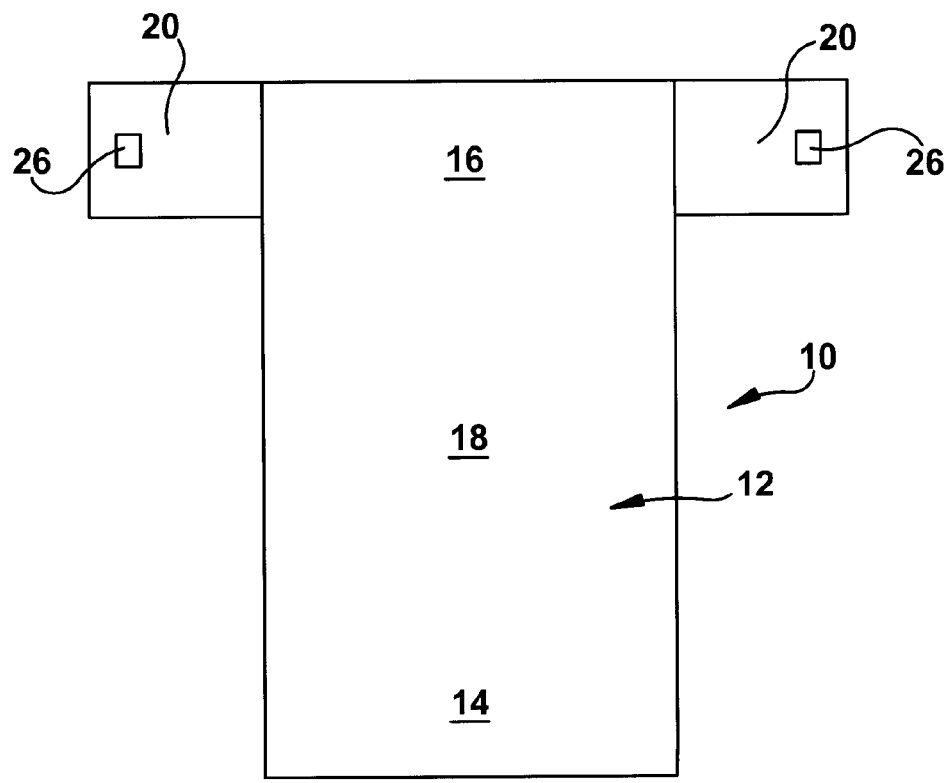
Figure 1E:
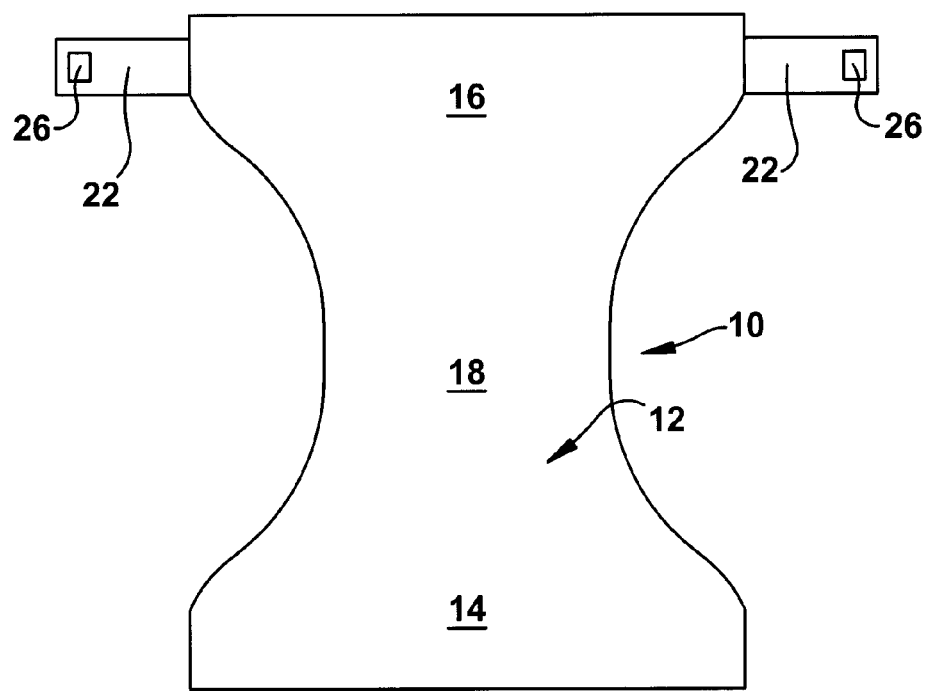

Alternatively, the side panel component 20 can carry the fastener 26 directly thereon (FIGS. 1B and 1D). If the diaper 10 does not include side panel components, the fastening tape components 22 can extend outward from each lateral edge of the rear chassis portion 16 (FIG. 1E). The fastener 26 can comprise any suitable fastening means (e.g., hooks/loops, snaps, adhesive/cohesive area(s), magnetic connections etc.) which allows selective attachment to an area on the front chassis portion 14. When diapering a wearer, the chassis crotch portion 18 is placed between his/her legs and the chassis rear portion 16 is fastened, via the fastener 26, to the chassis front portion 14 to form a waist around the wearer.

Figure 1F:
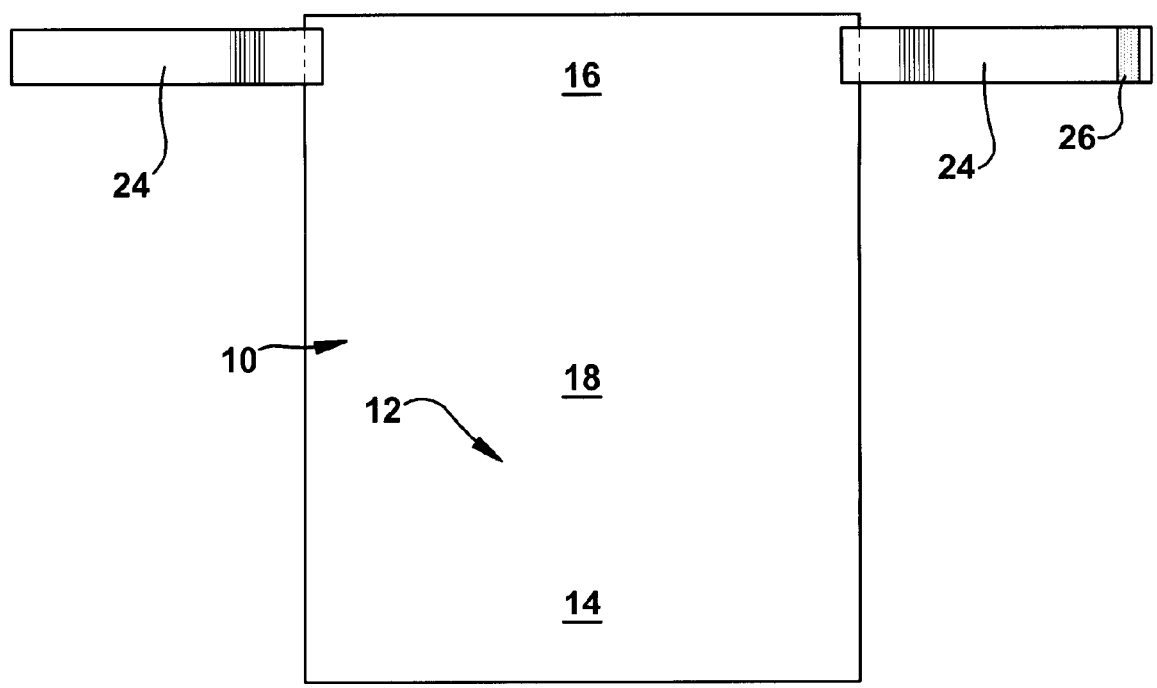
Figure 2A:
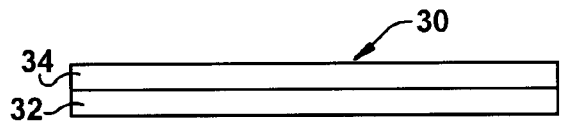
Figure 2B:
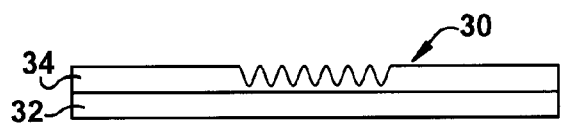
Figure 2C:
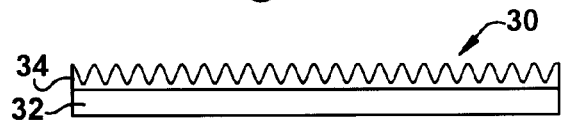
Figure 2D:
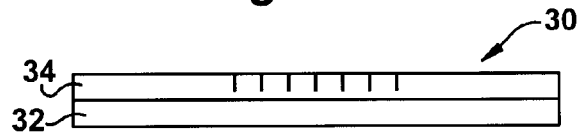
Figure 2E:
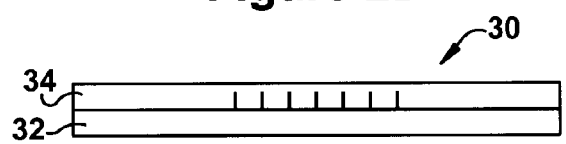
Figure 2F:
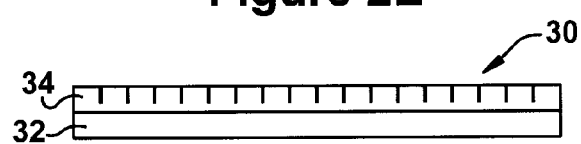
Figure 2G:
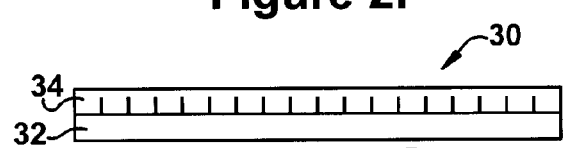
Figure 2H:
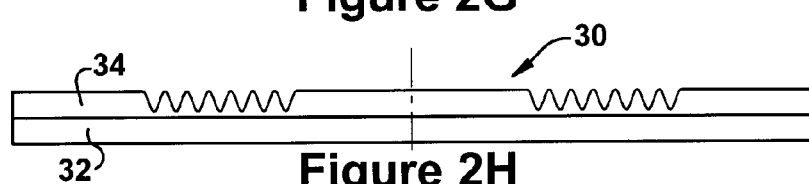
Figure 2I:
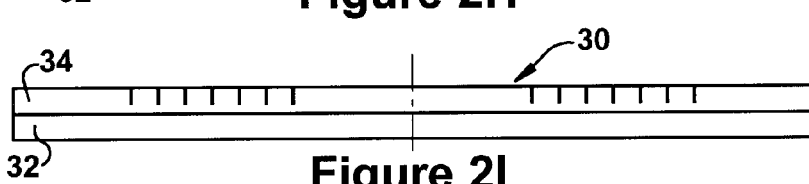
Figure 2J:
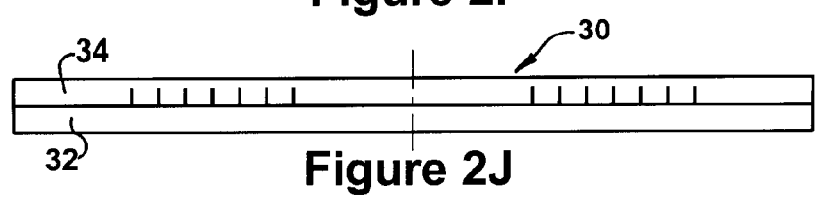
Figure 4A:
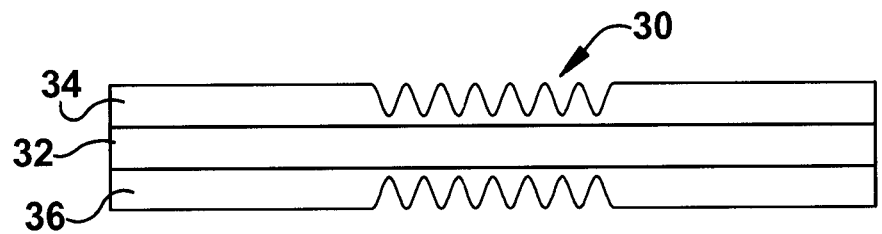
Figure 4B:
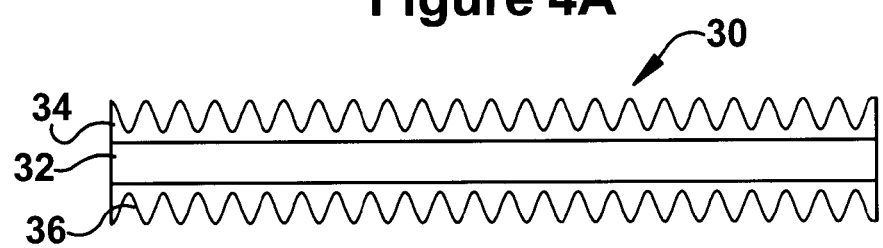
Figure 4C:
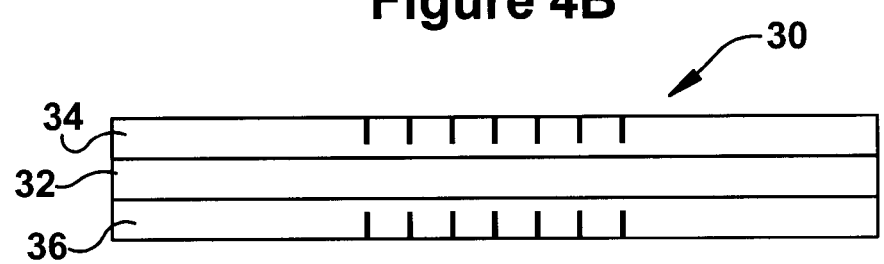
Figure 4D:
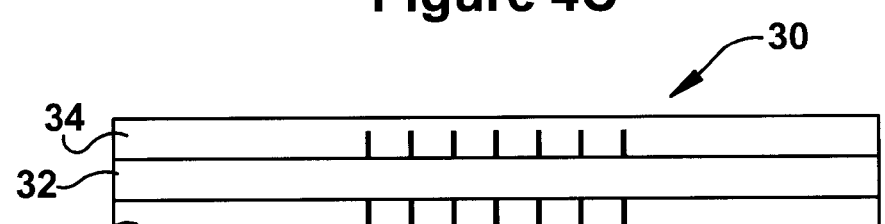
Figure 4E:
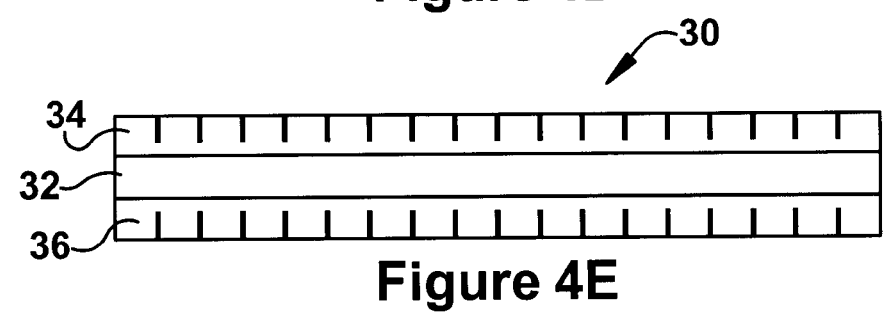
Figure 4F:
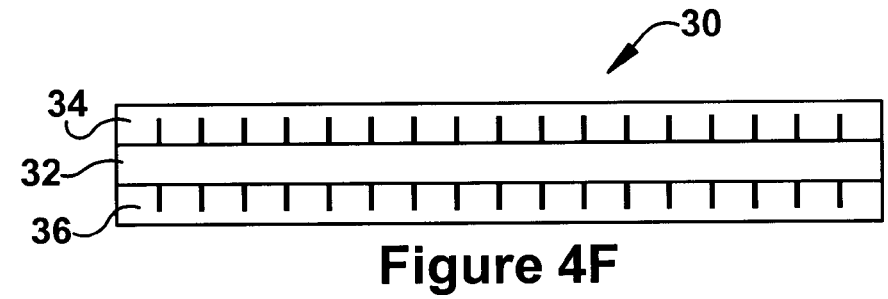
Figure 4G:
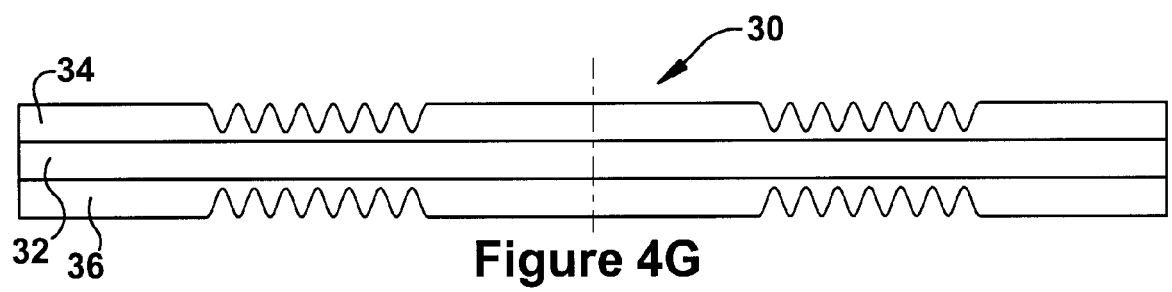
Figure 4H:
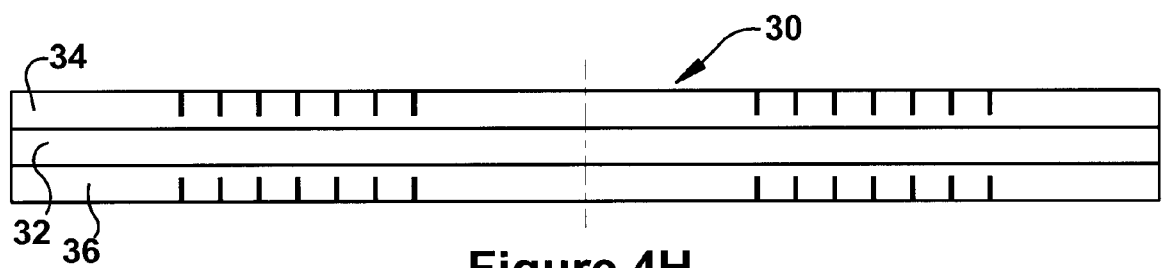
Figure 4I:
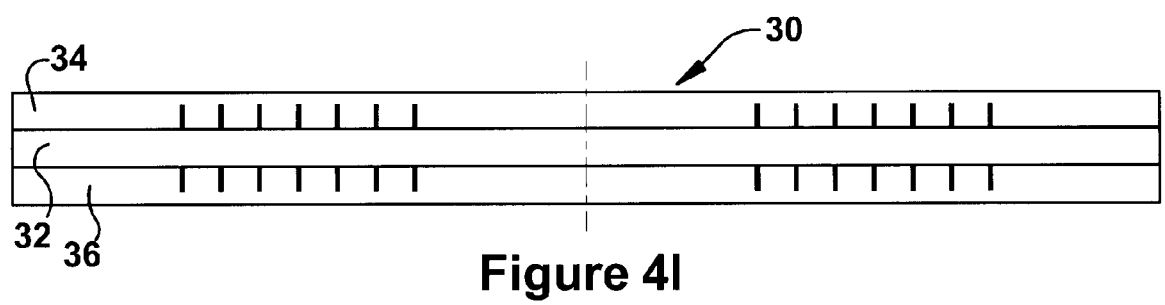

Instead of side panel components, the diaper 10 can include a belt component 24 attached to each lateral edge of the chassis rear portion 16 (FIG. 1F). One belt component 24 is folded around the user's waist (e.g., the left-hand belt in the illustrated diaper) and the other bel component 24 is then folded thereover. The belt components 24 are held in place by a fastener 26 carried by at least one of the belt components 24 (e.g., the right-hand belt in the illustrated diaper).

The side panel components 20, the fastening tape components 22, and/or the belt components 24 comprise elastic components whereby, during the diapering process, they can be stretched (e.g., it is pulled by the parent of the to-be-diapered baby) at a force $F_{fit}$ to an extended length and the respective fastener 26 fastened to the front chassis portion 14. Once fastened, and the fitting force $F_{fit}$ released, the recovery retraction force of the elastic component causes it to retract thereby snugly securing the diaper 10 around the wearer's waist. As the wearer's waist circumference expands and contracts during use of the diaper, the elastic component 20/22/24 extends and retracts to comfortably accommodate this movement while maintaining the snug fit of the diaper.

The illustrated diaper 10 is one in which the chassis front/rear portions 14/16 are attached together to form the waist during the initial fitting of the diaper. However, other diaper designs are possible and contemplated. For example, "pants-like" diaper designs could incorporate side panel components 20 and/or belt components 24 which are attached to the chassis front/rear portions 14/16 prior to the initial fitting. In this case, the relevant fitting force $F_{fit}$ can be that required to extend the components 20/24 when pulling the diaper up to the waist of the wearer (e.g., over his/her buttocks).

In a method of making the elastic diaper component 20/22/24, an elastic laminate 30 is provided, such as the laminates 30 shown in FIGS. 2A-2J, FIGS. 3A-3J, FIGS. 4A-4I, FIGS. 5A-5H or FIGS. 6A-6H. The thicknesses of the laminate 30 (and/or its layers 32/34/36 introduced below) are somewhat exaggerated in the drawings for the sake of clarity and explanation. If these thicknesses were drawn to scale with the illustrated lengths, it would probably be difficult to decipher and/or number the various layers. Also, with particular reference to FIGS. 5A-5H and FIGS. 6A-6H, these thicknesses may give the impression that certain aligned layer sections and/or areas are separated by spaces or gaps and do not contact one another. This may not be accurate as adjacent surfaces of neighboring layers in a laminate will generally be positioned flush against each other.

The elastic laminate 30 has a recoverable extension of at least 20% upon application of a corresponding extension force. The term "recoverable extension" refers to the ability of the laminate 30 to retract, via its inherent retraction recovery force, to substantially the same length (e.g., within 15%) upon release of the extension force. Thus, the elastic laminate 30 can be extended to a length representing at least a 20% increase (i.e., the extended laminate length will be equal or greater than 1.20 times the original laminate length) and return approximately to its original length upon release of the extension force. The potential recoverable extension of the elastic laminate 30 can, and will be in many cases, much higher than 20% (e.g., at least 50%, at least 100%, at least 200%, at least 300% etc.).

The laminate 30 can comprises an elastic layer 32 and a fabric layer 34 (FIGS. 2A-2G), or an elastic layer 32, a fabric layer 34, and another fabric layer 36 (FIGS. 3A-3G, FIGS. 4A-4F, FIGS. 5A-5D and FIGS. 6A-6D). The fabric layer 34 can be an elastic layer (FIG. 2A, FIG. 3A, FIG. 5A, and FIG. 6A), or the fabric layer 34 can be an inelastic layer (FIGS. 2B-2G, FIGS. 3B-3G, FIGS. 4A-4F, FIGS. 5B-5D, and FIGS. 6B-6D). The fabric layer 36 can be an elastic layer (FIGS. 3A-3G) or it can be an inelastic layer (FIGS. 4A-4F, FIGS. 5A-5D, and FIGS. 6B-6D).

If the fabric layer 34/36 is an inelastic layer, it can be manipulated to allow extension/retraction with the elastic layer 32. For example, the layer 34/36 may be mechanically manipulated by incremental stretching or "activation." (FIGS. 2B-2C, FIGS. 3B-3C, FIGS. 4A-4B, FIG. 5B and FIG. 6B.)

Additionally or alternatively, the layer 34/36 can be die-cut, kiss-cut, slit, scored, laser-cut, ultrasound-cut, or otherwise interrupted. (FIGS. 2D-2G, FIGS. 3D-3G, FIGS. 4C-4F, FIG. 5C-5D and FIGS. 6C-6D.) In the illustrated drawings, interruptions are schematically shown as being rather large for the purposes of simplicity. However, the interruptions can be spaced, for example, between 1 millimeter to 10 millimeters apart and can be evenly, or unevenly spaced, along the laminate.

The interruptions can extend partially through the layer thickness of the fabric layer 34/36 (e.g., 10% to 99%, 20% to 99%, 30% to 99%, 40% to 99%, 50% to 99%, 60% to 99%, 70% to 99%, and/or 80% to 99%), with tendons occupying the rest of the layer thickness. For example, if the interruption is a cut/slit/score, the tendon is the region of the cut/slit/score line which has not been cut/slit/scored.

If the elastic layer 32 is used as a reference layer, the fabric layer 34/36 will have a proximal side located closest to the elastic layer 32 and a distal side located away from the elastic layer 32. (The thickness of the fabric layer 34/36 is the distance between its proximal and distal sides.) The interruptions can be distal interruptions extending through the distal side of the fabric layer 34/36, (FIGS. 2D, 2F, 3D, 3F, 4C, 4E, 5C, and 6C) whereby the tendons would be proximal tendons extending from the proximal side of the fabric layer 34/36 to the aligned interruption. Alternatively, the interruptions can be proximal interruptions extending through the proximate side of the fabric layer 34/36 (FIGS. 2E, 2G, 3E, 3G, 4D, 4F, 5D and 6D) whereby the tendons would be distal tendons extending the rest of the way through the fabric. Although not specifically shown in the drawings, it may be possible for one fabric layer 34/36 to have distal/proximal interruptions while the other fabric layer 36/34 has proximal/distal interruptions, and/or for one fabric layer 34/36 to have both distal and proximal interruptions.

If the layer 34/36 is continuous across the width of the laminate 30 and the width of the elastic layer 32, the incrementally stretched or slitted portion can occupy only a section of the laminate width (FIGS. 2B, 2D and 2E, FIGS. 3B, 3D, and 3E, and FIGS. 4A, 4C, and 4D) or the increments/slits can occupy the entire laminate width (FIGS. 2C, 2F and 2G, FIGS. 3C, 3F and 3G, and FIGS. 4B, 4E, and 4F).

If the layer 34/36 is continuous across the width of the laminate 30, but not across the width of the elastic layer 32, the incrementally stretched or slitted portion can occupy only a section of the laminate width (FIGS. 5B-5D and FIGS. 6A-6D). For example, the incrementally stretched or interrupted portion can be aligned with the elastic layer 32 and coextensive therewith. The incrementally stretched or interrupted portion can not extend beyond the extent of the elastic layer 32 in the cross-direction C. The incremental stretches and/or interruptions can extend almost, but not quite the full cross-extent of the elastic layer 32 on each side, thereby leaving an unstretched/uninterrupted margin aligned with the elastic layer. This latter option may be desirable to, for instance, securely attached the elastic layer 32 to the fabric layers 34/36 when they are kiss-cut, die-cut, scored, slit, laser-cut, or ultrasound-cut, or otherwise interrupted. Margin widths in the range of 2-20 millimeters, 4-12 millimeters, and/or 6-10 millimeters may be sufficient for this purpose.

Figure 5A:
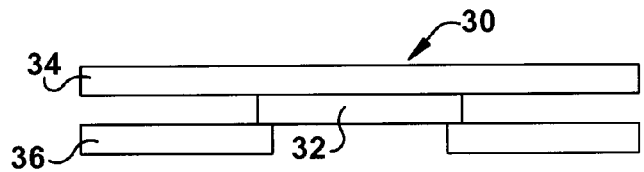
Figure 5B:
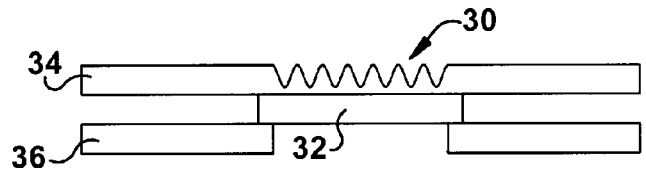
Figure 5C:
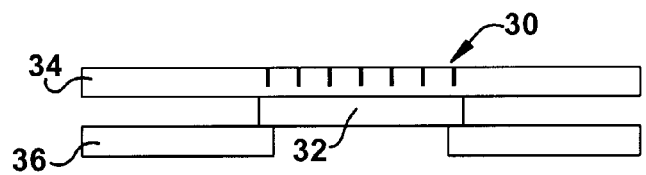
Figure 5D:
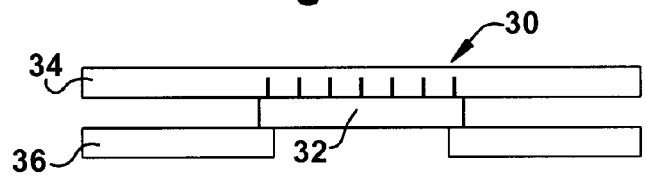
Figure 5E:
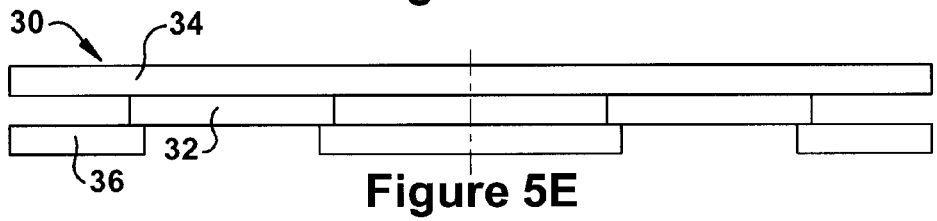
Figure 5F:
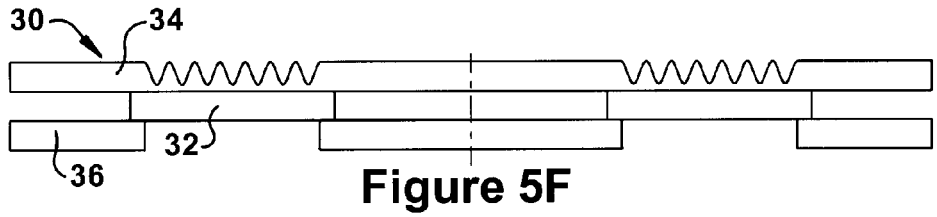
Figure 5G:
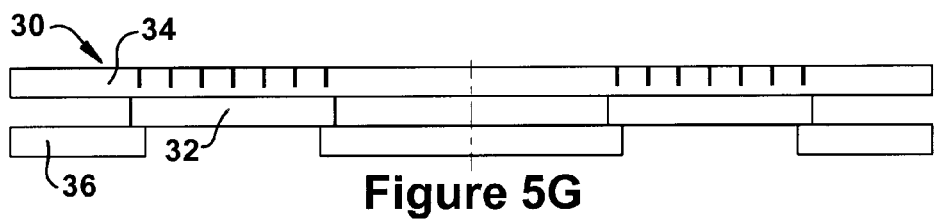
Figure 5H:
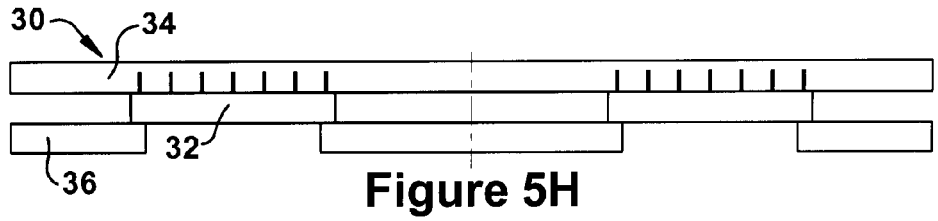
Figure 6A:
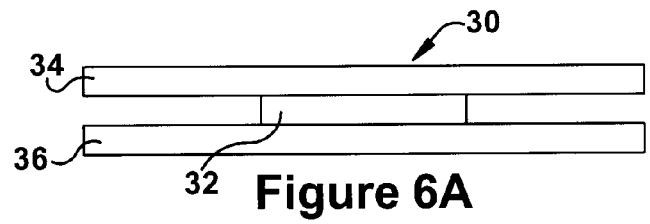
Figure 6B:
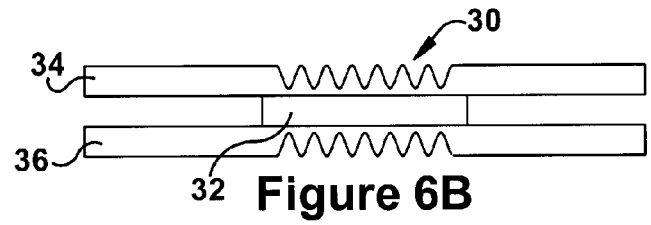
Figure 6C:
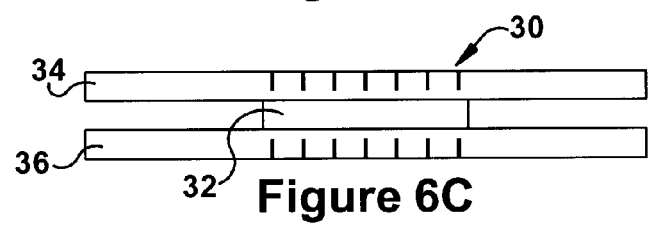
Figure 6D:
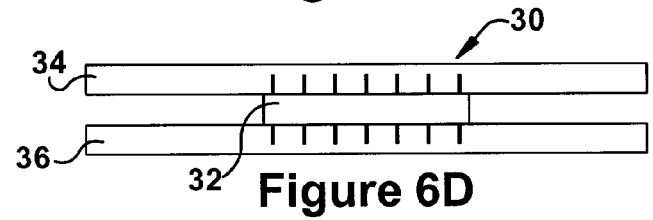
Figure 6E:
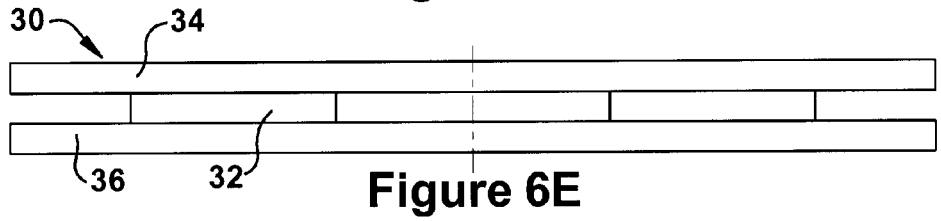
Figure 6F:
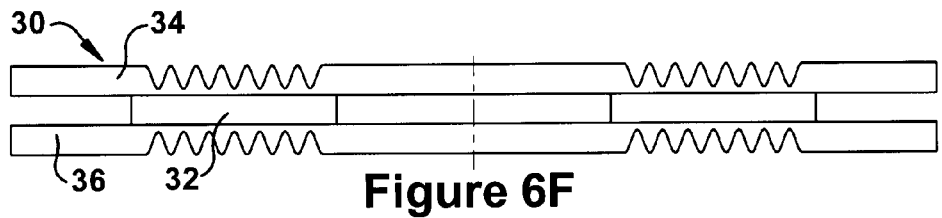
Figure 6G:
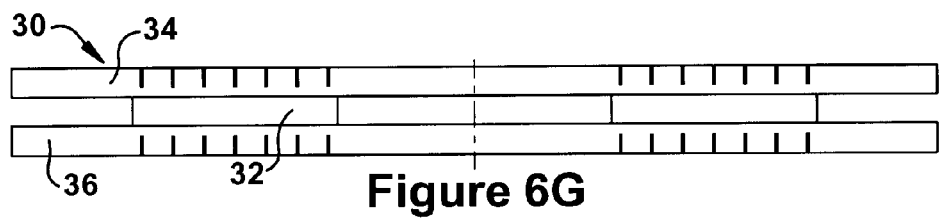
Figure 6H:
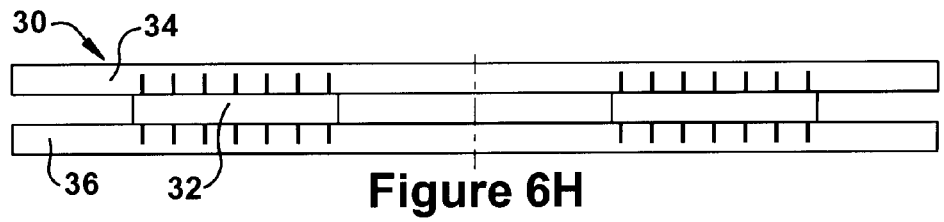

In the case where the incrementally stretched or slitted portion occupies a portion (e.g., a central portion) of the laminate width (FIGS. 2B, 2D and 2E, FIGS. 3B, 3D and 3E, FIGS. 4A, 4C, and 4D, FIGS. 5B, 5C and 5D, and FIGS. 6A, 6C, and 6D), a "double" laminate construction, such as shown in FIGS. 2H-2J, FIGS. 3H-3J, FIGS. 4G-4I, FIGS. 5F-5H, and FIGS. 6F-6H, may be adopted. A "double" laminate construction may also be useful when the elastic layer 32 and/or the fabric layer 36 is not continuous, as shown in FIG. 5E and FIG. 6E.

The elastic layer 32 can comprise a pre-formed film compiled with the fabric layers 34/36 or can comprise an extrudate extruded onto the fabric layers 34/36. In either or any event, the elastomer can be selected from the group consisting of styrene block copolymers, polyurethanes, polyesters, polyethers, and polyether block copolymers. Additionally or alternatively, the elastic layer 32 can comprise a vinyl arene-containing block copolymer (e.g., a block copolymer comprising SBS and/or SEBS).

The fabric layer(s) 34/36 can be nonwoven layers and they can be, for example, polyolefin, such as polyethylene and/or its copolymers, or polypropylene and/or its copolymers, or mixtures of the aforementioned polyolefins, polyurethanes, polyester, polyether or polyamide. The nonwoven materials can comprise, for example, spunbonded webs, meltblown webs, air laid layer webs, bonded carded webs, hydroentangled webs, wet-formed webs or any combination thereof.

The elastic laminate 30 is integratively pre-stretched to reduce the fitting force $F_{fit}$ required to extend the elastic component 20/22/24 to a desired length during an initial fitting of the diaper 10. This allows a wider range of elastic laminates (and probably some more economical laminates) to qualify as suitable candidates for the production of the elastic diaper components 20/22/24. Additionally or alternatively, less aggressive activation procedures may be used to produce original activated elastic laminates.

Figure 7:
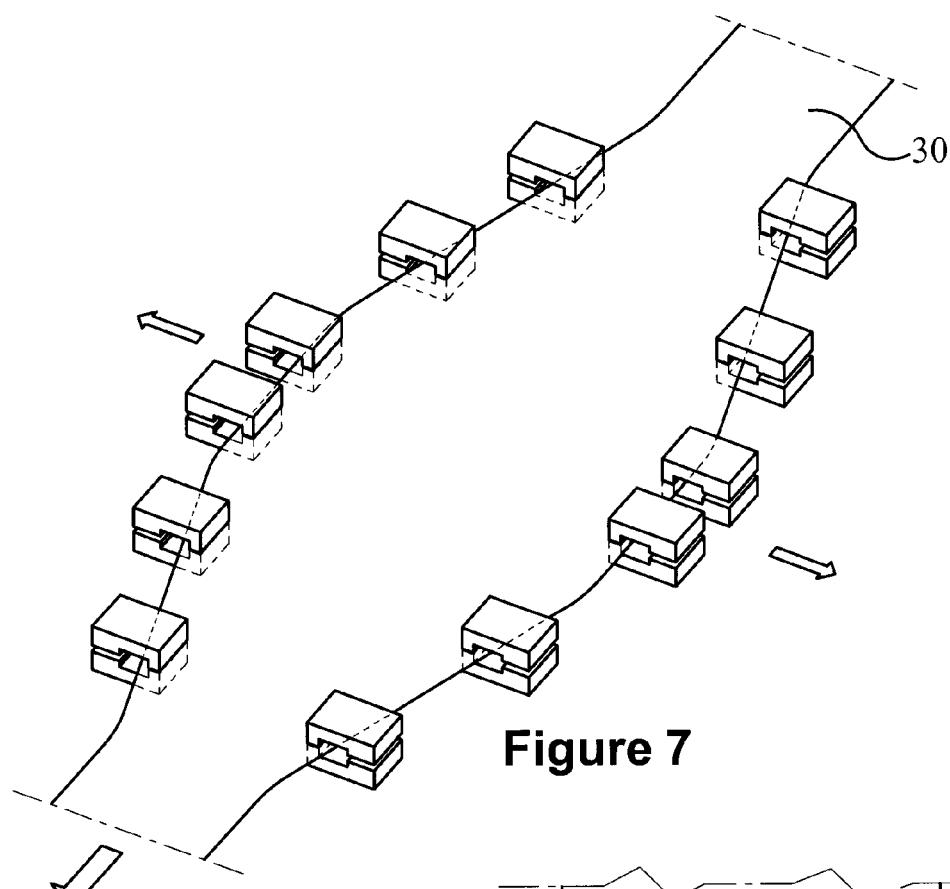
FIGS. 7-9 are schematic views of some of the possible integrative pre-stretching techniques.
Figure 8:
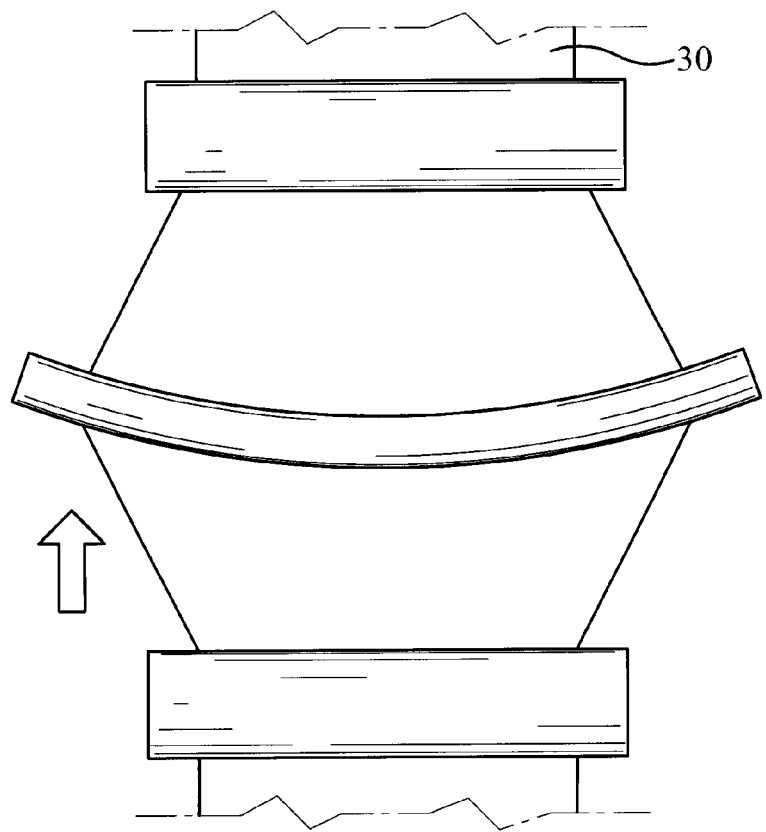
Figure 9:
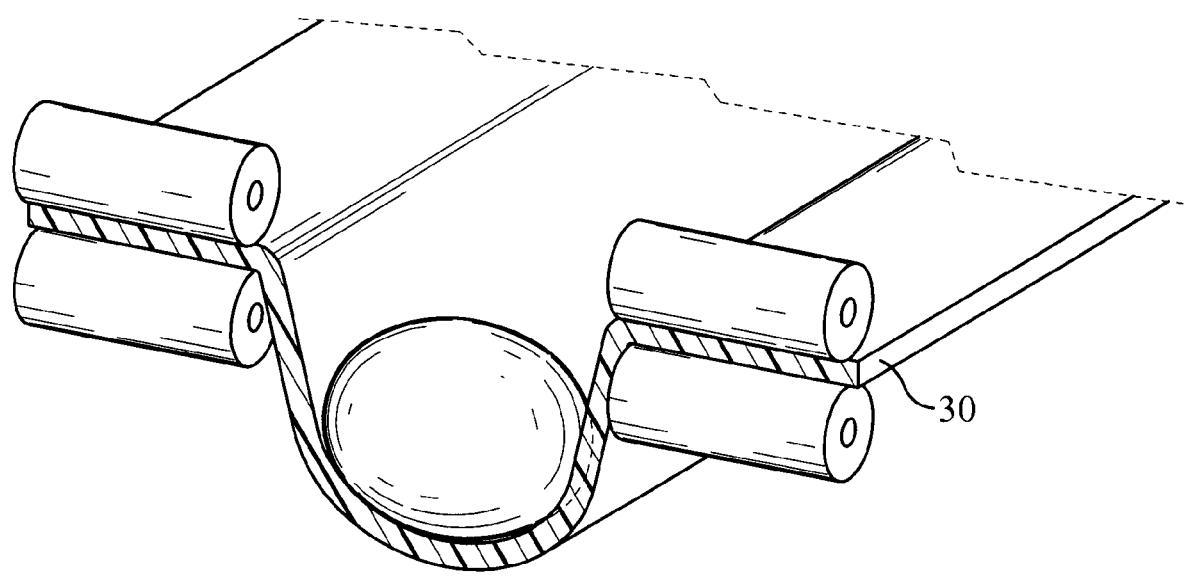

The pre-stretching step is "integrative" in that it stretches the laminate 30 in an amalgamated manner across its width (or portions of its width) as opposed to a sequence of small discrete stretching steps incrementally individually subjected to localized regions. The integrative pre-stretching step may be performed by gradually urging the elastic laminate 30 laterally outward to temporarily widen its span (FIG. 7), by causing the laminate 30 to travel through a curved route to temporarily widen its span (FIG. 8), or by conveying a portion of the laminate 30 through an offset path to temporarily widen its span (FIG. 9). In the latter technique, the integrative stretching is concentrated around a portion (e.g., the center portion) of the laminate 30 and it may be especially suitable for laminate constructions wherein a particular portion is intended to be rendered more elastic (FIGS. 2B, 2D and 2E, FIGS. 3B, 3D, and 3E, FIGS. 4A, 4C, and 4D, FIGS. 5B-5D, and FIGS. 6B-6D).

Figure 10A:
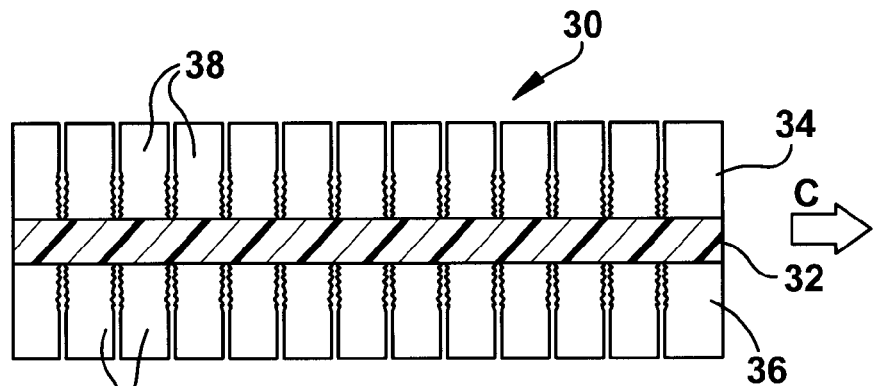
FIGS. 10A-10B are side views of an elastic laminate with distal severing and proximal severing, the laminate being shown in relaxed state in FIG. 10A and in an elongated state in FIG. 10B.

When the layer 34/36 is die-cut, kiss-cut, scored, laser-cut, ultrasound-cut, or otherwise interrupted (FIGS. 2D-2G, FIGS. 3D-3G, FIGS. 4C-4F, FIGS. 5C-5D, and FIGS. 6C-6D), the integrative pre-stretching step can comprise rupturing of at least some of the tendons. If such rupturing results in most and/or all of the tendons, the fabric layer 34/36 is divided into separable fabric segments 38/40 as is shown in FIGS. 10A-10B and FIGS. 11A-11B. The segments 38/40 may diverge upon laminate elongation, whereby the elastic layer 32 may be visible therebetween, (FIGS. 10B and 11B) and/or the segments 38/40 may converge upon laminate recovery, whereby the elastic layer 32 may be hidden thereby (FIGS. 10A and 11A).

The fabric-segmenting seams (a seam being formed by the combination of an interruption and an aligned rupture) will constitute an interrupted region and a ruptured region. (FIG. 10C and FIG. 11C.) With distal interruptions (FIGS. 2D and 2F, FIGS. 3D and 3F, FIGS. 4C and 4E, FIG. 5C, and FIG.

Figure 10B:
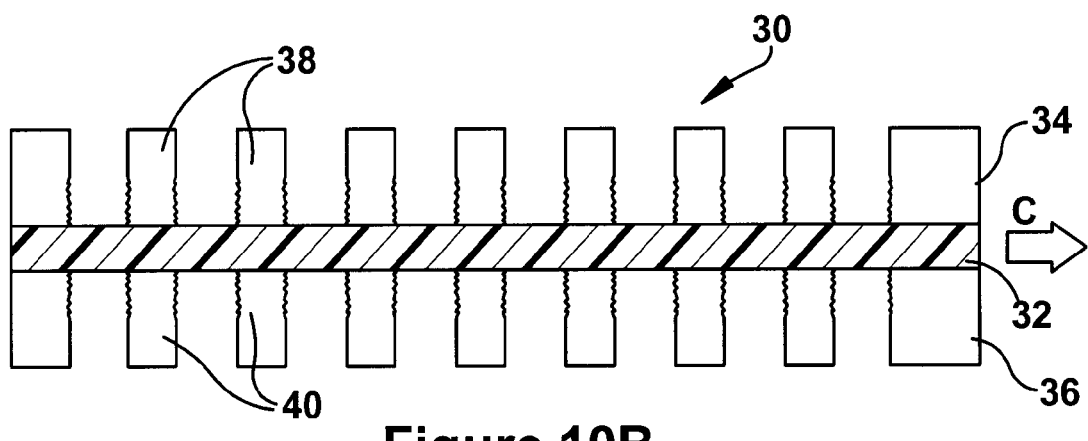
Figure 10C:
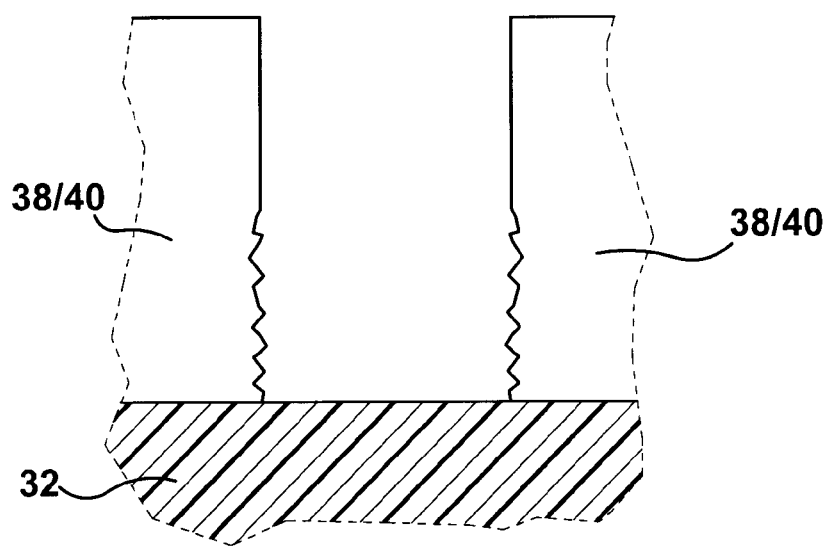
FIG. 10C is a close-up view of severed/ruptured regions of the elastic laminate of FIGS. 10A-10B.
Figure 11A:
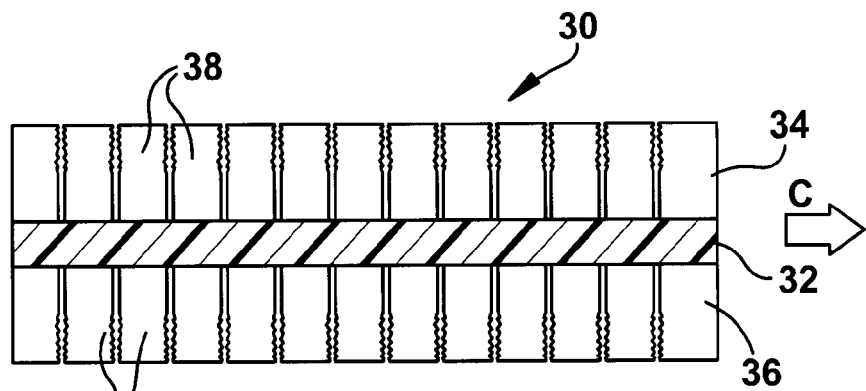
FIGS. 11A-11B are side views of an elastic laminate with proximal severing and distal rupturing, the laminate being shown in relaxed state in FIG. 10A and in an elongated state in FIG. 10B.
Figure 11B:
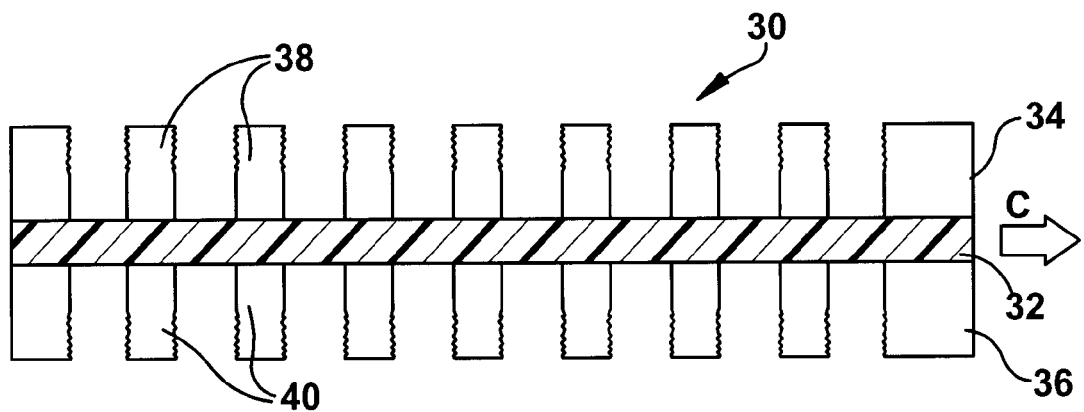
Figure 11C:
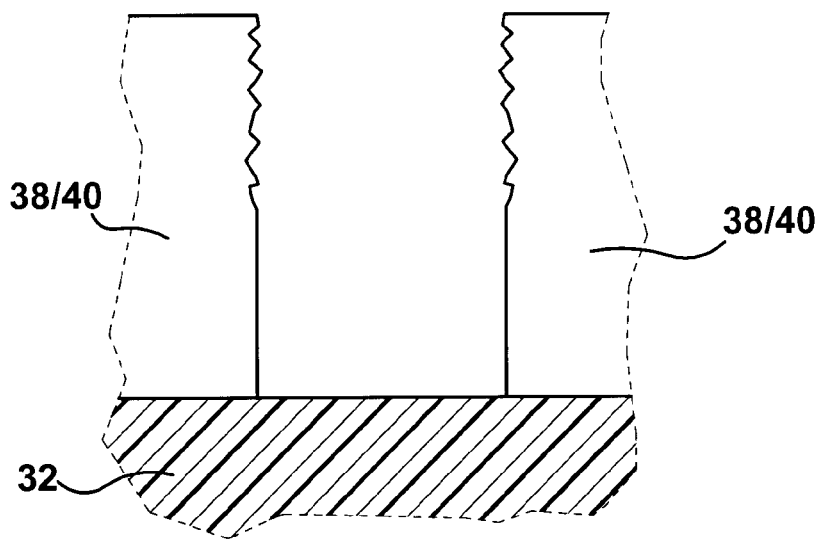
FIG. 11C is a close-up view of severed/ruptured regions of the elastic laminate of FIGS. 11A-11B.

6C), the ruptured region will be a proximal region (FIGS. 10A-10C). With proximal interruptions (FIGS. 2E and 2G, FIGS. 3E and 3G, FIGS. 4D and 4F, FIG. 5D, and FIG. 6D), the ruptured region will be a distal region (FIGS. 11A-11C). If the interrupted region is die-cut, kiss-cut, slit, scored, laser-cut, or ultrasound-cut, or otherwise sharply split, it will be defined by primarily severed fabric strand ends, that is fabric strand ends which have been severed cleanly and neatly, as shown schematically in FIG. 12A. The rupture regions will, in contrast, be defined by primarily fractured fabric strand ends, that is fabric strand ends which have been broken roughly and/or unevenly, as shown schematically in FIG. 12B.

If the elastic laminate 30 is to be used to make the side panel components 20, the laminate 30 can be separated into side panel shapes and the side panel components 20 secured to the diaper chassis 12 to incorporate them into the diaper 10. If the elastic laminate 30 is to be used to make the fastening tape components 22, the laminate 30 can be separated into fastening shapes and the fastening components 22 secured to the appropriate surface (e.g., the side panel 20 or the chassis 12) to incorporate them into the diaper 10. If the elastic laminate 30 is to be used to make the belt components 24, the laminate 30 can be separated into belt shapes and secured to the diaper chassis 12. The separating step and/or the securing step can be performed after the integrative stretching step. In any event, the integrative pre-stretching step is performed prior to the initial fitting of the diaper 10 on a wearer and the elastic component 20/22/24 is in a relaxed (i.e., unstretched) state until the fitting process begins.

Referring now to Graphs 1-3, the two cycles of extension forces E and retraction forces R for three different elastic laminate constructions are plotted in relation to extension percentage. Graph 1 reflects data obtained with an elastic laminate 30 comprising an elastic film layer 32 and inelastic nonwoven layers 34/36 which are activated by incremental stretching. (See e.g., FIG. 4A, above.) Graph 2 reflects data obtained from a similar elastic laminate 30, except with a thinner elastic film layer 32. Graph 3 reflects data obtained from an elastic laminate 30 comprising an elastic film 32 and elastic nonwoven layers 34 and 36. (See e.g., FIG. 3A, above.)

The Graphs 1-3 each include an upper (greater) extension force $E_1$ curve and a lower (lesser) extension force $E_2$ curve. The upper curve corresponds to the stretch characteristics prior to integrative pre-stretching and the lower curve corresponds to stretch characteristics after integrative pre-stretching at 200%. As was indicated or alluded to above, an elastic laminate (prior to or without integrative pre-stretching) will have a recoverable extension of at least 20% upon application of a corresponding extension force $E_1$.

If a non-pre-stretched elastic laminate was used as the elastic diaper component 20/22/24, the fitting force $F_{fit}$ required to extend the elastic component 20/22/24 to a desired length during an initial fitting of the diaper 10 on a wearer would correspond to the upper $E_1$ extension force curve. When a pre-stretched elastic laminate is used as the diaper component 20/22/24, the required fitting force $F_{fit}$ corresponds to the lower $E_2$ extension force curve.

For each elastic laminate, the first cycle extension forces $E_1$ are higher than the second cycle extension forces $E_2$ for the same recoverable extensions. With the laminate 30 plotted in Graph 1, the original elastic laminate (i.e., prior to pre-stretching) required an extension force $E_1$ of over 10N to reach a 100% extension, while the extension force $E_2$ required to extend the pre-stretched elastic component 20/22/24 to this same length would be just over 5N. With the laminate 30 plotted in Graph 2, the extension force $E_1$ is about 5N and the extension force $E_2$ is about 2N to reach a 100% extension. With the laminate 30 plotted in Graph 3, the corresponding not-pre-stretched and pre-stretched values are over 6N and less than 3N for a 100% elongation.

Graphs 1-3 also reflect that the recovery retraction forces $R_1$ and $R_2$ for the first cycle and the second cycle are substantially the same. Thus, the pre-stretched elastic laminate retracts in much the same manner as the original elastic laminate. In this manner, the pre-stretched component 20/22/24 can snugly secure the diaper around the wearer's waist during the initial fitting and can adequately retract to accommodate contraction of the wearer's belly (or other decreases in waist circumference) during use of the diaper.

In the first cycle curves, the extension forces $E_1$ gradually increase (i.e., the slope of the curve is linear) throughout material extension. In the second cycle curves, however, the extension forces $E_2$ gradually (i.e., linearly) increase in the early stages of material extension and then more sharply incline as the extension percentages increase. (In the illustrated graphs, this increase occurs above about 140%, however this will vary depending upon the elastic laminate, pre-stretching conditions, and/or other factors.) When an integratively pre-stretched elastic component 20/22/24 is used, the reflexive reaction to a sudden increase in resistance will typically be to cease extension of the component 20/22/24. Thus, a fitting force $F_{fit}$ will usually not extend beyond the linearly-sloped region of the $E_2$ curve. This can help prevent over-extension of the component 20/22/24 during the diapering process (and the corresponding compromise of elastic recoverable extension properties). Also, the linearly sloped region of the $E_2$ curve corresponds to the linearly sloped region of the $R_2$ curve, whereby retraction during use of the diaper 10 will also be gradual.

Graphs 4-6 are each a plot of hysteresis curves showing two cycles of extension forces E and retraction forces R for the same elastic laminate construction, with Graph 4 showing these forces without integrative pre-stretching the elastic laminate, Graph 5 showing these forces after integratively pre-stretching the elastic laminate 100%, and Graph 6 showing these forces after integratively pre-stretching the elastic laminate 150%. In each of these graphs, the first cycle extension forces $E_1$ would correspond to the fitting force $F_{fit}$ and the second cycle extension forces $E_2$ would correspond to the extension forces during use of the diaper (e.g., when the wearer's belly expands). Graphs 4-6 demonstrate that the magnitude/profile of the reduction of the extension force $E_2$ due to integrative pre-stretching can differ depending upon the degree of pre-stretching (e.g., 50%, 100%, 150%, 200%, etc.). In any or every event, the pre-stretching extension should not exceed the upper recoverable extension limit of the elastic laminate.

One may now appreciate that integrative pre-stretching of an elastic laminate can reduce required fitting forces for the elastic component 20/22/24 during the initial fitting of the diaper, facilitate comfortable waist extensions/retractions of the component 20/22/24 during use of the diaper, allow production of the component 20/22/24 from a wider range of elastic laminates, and/or guard against over-extension of the component 20/22/24.

Although the diaper 10, the components 20/22/24, the laminate 30, the method, and/or method steps have been shown and described with respect to certain embodiments, equivalent alterations and modifications will occur to others skilled in the art upon the reading and understanding of this specification and the annexed drawings. In regard to the various functions performed by the above described elements (e.g., components, assemblies, systems, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function. In addition, while a particular feature may have been described above with respect to only one or more of several illustrated embodiments, such features may be combined with one or more other features of the other embodiments, as may be desired and advantageous for any given or particular application.

The invention claimed is:

1. A method of making an elastic diaper component, comprising the steps of:
    providing an elastic laminate including an elastic layer and a first fabric layer, wherein the elastic laminate has a recoverable extension of at least 20% when an extension force E1 is applied; and
    integratively pre-stretching in an amalgamated manner across a width of the elastic laminate so that the elastic laminate will stretch to the same recoverable extension when a reduced extension force E2 is applied; manner wherein the integratively pre-stretching step comprises urging the elastic laminate laterally outward to temporarily widen its span, causing the elastic laminate to travel through a curved route to temporarily widen its span, and/or conveying a portion of the elastic laminate through an offset path to temporarily widen its span;
    whereby, when the elastic laminate is used in the elastic diaper component, a lesser fitting force $F_{fit}$ is required to extend the elastic component to a desired length during an initial fitting of a diaper on a wearer, compared to the fitting force required to extend an elastic diaper component comprising a laminate that has not been pre-stretched.

2. A method as set forth in claim 1, wherein the integrative pre-stretching step comprises an at least 100% extension of the elastic laminate.

3. A method as set forth in claim 2, wherein the first fabric layer is an inelastic nonwoven layer.

4. A method as set forth in claim 3, wherein the elastic laminate comprises a second fabric layer and wherein the elastic layer is positioned between the two fabric layers.

5. A method as set forth in claim 4, wherein the second fabric layer is an inelastic nonwoven layer.

6. A method as set forth in claim 4, wherein the first fabric layer and/or the second fabric layer is mechanically manipulated prior to said integrative pre-stretching step to allow it to extend/retract with the elastic layer.

7. A method as set forth in claim 4, wherein the first fabric layer and/or the second fabric layer have interruptions formed therein prior to said integrative pre-stretching step; wherein:
    the interruptions extend partially through the layer thickness of the fabric layer and tendons extend through the rest of the layer thickness;
    the interruptions extend 50% to 99% through the thickness of the fabric layer;
    the interruptions comprise die-cuts, kiss-cuts, slits, scores, laser-cuts, and/or ultrasound-cuts;
    the interruptions are distal interruptions and the tendons are proximal interruptions;
    and wherein said integrative pre-stretching step comprises rupturing at least some of said tendons.

8. A method as set forth in claim 7, wherein said rupturing step results in the fabric layer being divided into separable fabric segments which diverge upon elongation and converge upon recovery.

9. A method as set forth in claim 1, wherein said integratively stretching step comprises stretching the elastic laminate in an amalgamated manner across portions of its width.

10. A method as set forth in claim 1, further comprising the step of separating the elastic laminate into side panel shapes, fastener tape shapes, or belt shapes.

11. A method as set forth in claim 10, wherein said separating step is performed after said integrative stretching step.

12. A method comprising incorporating a pre-stretched component made by the method set forth in claim 11 into a diaper, wherein said integrative pre-stretching step is performed prior to said incorporation.

13. A method comprising the steps of providing an elastic laminate and integratively pre-stretching in an amalgamated manner across a width of the elastic laminate; wherein the integratively pre-stretching step comprises urging the elastic laminate laterally outward to temporarily widen its span, causing the elastic laminate to travel through a curved route to temporarily widen its span, and/or conveying a portion of the elastic laminate through an offset path to temporarily widen its span;
    wherein the laminate comprises an elastic layer and at least one fabric layer laminated thereto;
    wherein the fabric layer has interruptions formed therein prior to said integrative prestretching step;
    wherein the interruptions extend partially through the layer thickness of the fabric layer and tendons extend the rest of the way through the fabric thickness; and
    wherein said integrative pre-stretching step comprises rupturing at least some of said tendons and dividing the fabric layer into separable fabric segments which diverge upon elongation and converge upon recovery.

14. A method as set forth in claim 13, wherein the interruptions extend 50% to 99% through the thickness of the fabric layer; wherein the interruptions comprise die-cuts, kiss-cuts, slits, scores, laser-cuts, and/or ultrasound-cuts; and wherein the interruptions are distal interruptions and the tendons are proximal interruptions.

* * * * *